United States Patent [19]

Ronge

[11] Patent Number: 5,056,511

[45] Date of Patent: Oct. 15, 1991

[54] METHOD AND APPARATUS FOR COMPRESSING, ATOMIZING, AND SPRAYING LIQUID SUBSTANCES

[75] Inventor: Georg Ronge, Munich, Fed. Rep. of Germany

[73] Assignees: Juergen L. Fischer, Tegna, Switzerland; Manfred Buesselmann, Paris, France

[21] Appl. No.: 450,598

[22] Filed: Dec. 14, 1989

[51] Int. Cl.⁵ .................. A61M 11/00; A61M 11/06; B05B 9/047; B05B 9/04

[52] U.S. Cl. .................. 128/200.14; 128/200.23; 128/203.12; 128/203.23; 261/78.2; 239/338; 239/324

[58] Field of Search ............ 128/200.14, 200.22, 128/203.12, 200.23, 203.23; 239/1, 8, 320, 321, 323, 324, 337, 338; 261/78.2

[56] References Cited

U.S. PATENT DOCUMENTS

| | | | |
|---|---|---|---|
| 58,118 | 9/1866 | Farland | 239/320 |
| 1,044,985 | 11/1912 | Bullen | 239/320 |
| 1,208,341 | 12/1916 | Loftus | 261/78.2 |
| 1,342,580 | 6/1920 | Bastian | 239/324 |
| 2,880,939 | 4/1959 | Esmay | 239/320 |
| 3,666,245 | 5/1972 | Edwardson | 239/337 |

FOREIGN PATENT DOCUMENTS 821322 11/1951 Fed. Rep. of Germany ...... 239/321

Primary Examiner—Edgar S. Burr
Assistant Examiner—Kimberly L. Asher
Attorney, Agent, or Firm—Hedman, Gibson, Costigan & Hoare

[57] ABSTRACT

The method and apparatus for atomizing and spraying liquid substances serves in particular to produce clouds for inhalation purposes. The liquid substance to be atomized is compressed to such an extent that it decreases in volume and that it is then explosively released into the normal atmosphere. Due to its high internal pressure, the liquid substance bursts into extremely small particles.

25 Claims, 1 Drawing Sheet

METHOD AND APPARATUS FOR COMPRESSING, ATOMIZING, AND SPRAYING LIQUID SUBSTANCES

BACKGROUND OF THE INVENTION

1. Field of the Invention

The invention relates to a method and an apparatus for atomizing and spraying liquid substances for inhalation purposes.

2. Description of Related Art

In known aerosol production methods aerosols have been produced by means of an air stream, by fans or centrifugal atomizers. Known inhalation methods have been used to transport by inhalation the essence of a liquid substance after conversion into an aerosol to the surface of the bronchi and bronchioles, where the atomized liquid has a therapeutic effect.

It is an object of the present invention to provide a novel method and apparatus for atomizing and spraying liquid substances wherein the particles are excellently absorbed by inhalation.

SUMMARY OF THE INVENTION

In accordance with the method and apparatus of the present invention, the liquid body to be atomized is compressed to such a degree that it decreases in volume. Unlike in gases, compression causing a change in volume can only be achieved in liquids by applying a very high pressure, i.e., between 300 and $800 \times 10^5$ Pa. When the thus compressed liquid body is released into the normal atmosphere of $10^5$ Pa (1 bar) the liquid body, due to its high internal pressure, explodes into extremely small particles dispersing in all directions and atomizes to a very fine cloud.

The liquid substance to be atomized preferably contains vitamins, in particular vitamins A, B, C and/or E, and, in addition, optionally lecithin. Suitable dosages of the mentioned vitamins and lecithin are dissolved in a liquid such as water, preferably oil.

In accordance with the invention, especially liquids having high viscosities, in particular oils, which could not be sufficiently sprayed by previous known methods can be atomized to extremely fine particles. In particular, oily or oil-dissolved substances such as vitamins A and E can be atomized.

It is preferable to spray vegetable oil such as peanut oil in which vitamins, e.g., A and E are contained.

Advantageously, the liquid substance contains 0.5 to 5% by weight of vitamin A and/or 0.5 to 5% by weight of vitamin E. More preferred is a blend of peanut oil with 2.5 % by weight of vitamin A acetate and 4% by weight of vitamin E tocopherol.

Particularly preferred is a blend of peanut oil with 1.25% by weight of vitamin A acetate and 0.5% by weight of vitamin E tocopherol.

In accordance with the invention, the substance to be atomized is compressed at a pressure of 300 to $800 \times 10^5$ Pa. The adjusted pressure is dependent on the liquid substance to be atomized. When a certain pressure is exceeded, the individual liquid changes state, that is, its volume is reduced. Liquid substances having higher viscosities require a higher pressure. The pressure required for spraying liquid substances is in the range of 500 and $800 \times 10^5$ Pa for viscous liquids, e.g., organic oils. For aqueous liquids, e.g., salt solutions, a pressure of 300 to $500 \times 10^5$ Pa, preferably $430 \times 10^5$ Pa, is adjusted.

If a liquid is compressed at too low a pressure, e.g., $100 \times 10^5$ Pa only, no explosive atomization of the substance will occur, instead a closed jet of the liquid will be emitted from the nozzle as in a diesel injection engine. By selecting the suitable pressure depending on the viscosity of the liquid substance, the desired cloud instead of the diesel jet can be obtained.

When a voltage is applied to a high-voltage electrode in front of the nozzle of a compression apparatus, the conductivity, for example, of a salt-containing liquid jet immediately leads to a voltage collapse. However, if the liquid is atomized in accordance with the method of the present invention, the thus sprayed liquid body, after passing the opening of the compression space, will not even have a break-down effect directly at the outlet, and when salt-containing liquids are sprayed, a high-voltage electrode which is placed directly in front of the opening of the compression space will not lose any voltage with respect to the compression apparatus.

The method of the present invention comprises producing particles having a size of about 0.5 to 10 $\mu m^3$, preferably about 1 $\mu m^3$, which means that 1 $\mu m^3$ of liquid bursts into one billion ($10^9$) particles. In accordance with the invention, the resultant particles have a potential which is equal for all the particles, so that the particles repel each other in the cloud. The potential of the particles, i.e., the atomized liquid droplets is different from that of the medium, and the droplets are preferably charged positively.

The method of the present invention can be carried out until the desired amount of liquid substance is atomized. According to a preferred embodiment of the invention, after compressing the liquid substance to be atomized, only a portion of about 0.25 ml is released into the normal atmosphere and thereby atomized, this procedure being repeated several times, e.g., 200 times.

The apparatus of the present invention comprises a compression space which will stand the pressure of the liquid to be compressed, and which has one or more small openings. Also, with the liquid having a certain internal pressure of, for example, 600 to $800 \times 10^5$ Pa (1 bar) when passing these openings, the pressure of the liquid in the interior of the compression space does not fall below a desired pressure of, for example, $550 \times 10^5$ Pa. Thus, when passing the fine openings, the liquid introduced into the compression space explosively bursts into the desired cloud particles due to the high drop of pressure. The pressure is generated by a high-pressure pump which conveys the liquid substances to the compression space via a pipe.

In accordance with the invention, these controllable nozzles automatically open at an upper pressure and automatically close again at a lower pressure. The upper limit is adjustable preferably between 500 and $800 \times 10^5$ Pa, the lower limit preferably between 200 and $600 \times 10^5$ Pa.

Preferably, the size of the compression space is adjustable, resulting in the amount of released liquid to be atomized being variable at a specifically adjusted upper and lower pressure.

According to a further embodiment of the invention, the controllable nozzle is arranged at the entrance side of a cloud chamber such that the liquid to be atomized is released into the cloud chamber. The cloud chamber is preferably a cylinder with a bottom and a top. Furthermore, an air inlet and outlet are provided at the cloud chamber which have a sound absorber each. The cloud chamber serves, on the one hand, to evenly disperse the atomized liquid and, on the other, to provide sound insulation for the nozzle device. Preferably, a suitable mouthpiece or breathing funnel is arranged at the outlet, through which the atomized liquid can be inhaled.

In a further embodiment a non-return valve is arranged in the mouthpiece, which opens only when air is sucked from the cloud chamber. It blocks in the other direction, thereby preventing air from outside, for example, expired air from getting into the cloud chamber. This advantageously avoids that impurities get into the cloud chamber.

The method and apparatus of the present invention have the particular advantage of producing a very fine cloud for inhalation with which the substance suitable for therapy can be breathed in directly. Thus, substances of all kinds, even highly viscous organic oils and the substances dissolved therein, can be transported to the surface of the alveoli, the air pockets in the lungs. These substances are absorbed, resorbed, so-to-speak "digested" by those, thus getting directly into the arterial blood.

The lungs are excellent digestive organs of the living organism. Similar to the huge surface of the leaves of plants, they allow direct absorption of substances in the air. This makes it possible, while completely avoiding the entire digestive tract, to introduce substances into the arterial bloodstream, which can thus be transported to any organ and any place in the organism. By inhalation of very thick and concentrated clouds of liquid substances, active amounts of substance can shortly, for example, already after some breaths, in 1 minute or so, be transported to the alveoli and then directly to the bloodstream.

The present invention has the advantages that the droplets are incomparably respirable due to the fineness of the cloud, that the density of the cloud can be controlled and that the amount of liquid to be sprayed is practically not limited.

The present invention is characterized in particular by the existing technical effect that there is a particular attraction (affinity) between the atomized liquid droplets, on the one hand, and the lung alveoli, on the other, due to a difference in potential. Because of this attraction the droplets are excellently absorbed by the alveoli. The droplets are preferably charged positively, while the cells of the lung alveoli are charged negatively. The smaller the droplets, the greater will be the effect of attractive power. For one thing, the movability of the droplets is greater, for the other, the charge per mass unit is greater.

The method of the present invention makes it possible to transport 15 ml of the liquid substance to be atomized to the alveoli within one minute, where they are absorbed and resorbed. Substantial part of the total amount of substance inhaled adheres to the bronchial vessels and is absorbed thereby, while a minor part leaves the lungs during expiration in the form of very fine, smoky "vapor".

The "alternative" route of administration of substances via the digestive tract containing substance-converting gastric juices and enzymes—stomach, pancreas, liver, gall —is avoided, so that the substance is transported "without difficulty" and unchanged to all organs and systems of the entire organism. If the aforementioned digestive routes are to be avoided, there has so far merely been the possibility of injection. This method of application is known to forbid the introduction of oily substances. The method of the present invention makes it possible to convey in particular oil-soluble substances to the organism without difficulty. For instance, vitamins, e.g., A and B, in a possibly diffuse, mainly molecular form, can be conveyed to internal organs, especially to epithelia and connective tissue, and to nervous and central-nervous systems. Foci of infection in the organism can be therapeutically treated by inhalation of the cloud of vegetable oil, e.g., peanut oil comprising the dissolved vitamins A and E as provided in accordance with the invention. Experiments have confirmed the effectiveness of the method and the apparatus of the present invention. The method of the present invention is also suitable for the production of an inhalation cloud for the treatment of the bronchi and bronchioles, for asthmatic diseases and other illnesses which are difficult to treat. The method can further be used for inhalation of substances which lead to a substantial improvement in the overall physical condition, painlessness and sleep fastness, and an enhancement of the physical and mental performance of the patient. The method has a central effect throughout the organism. The method of the present invention is also excellent in atomizing and spraying water-soluble substances in water. The blend can be sprayed for inhalation purposes, such as, for example, sea salt solutions or brines in seaside resorts and in the sauna, and to intensify the saline effect.

The invention is hereinbelow further illustrated by an example and a drawing.

DESCRIPTION OF THE PREFERRED EMBODIMENT

Figure 1:
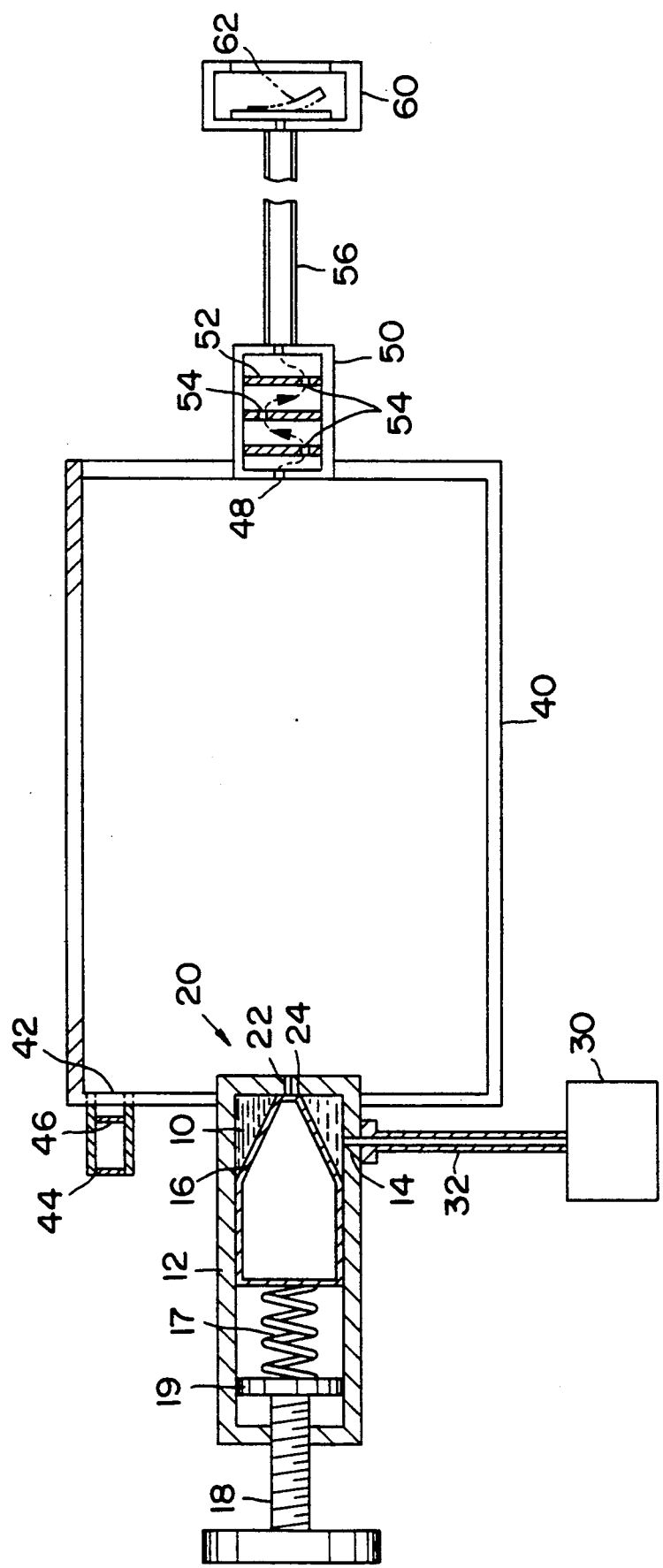
FIG. 1 shows a preferred embodiment of the apparatus of the present invention.

The depicted preferred embodiment comprises a compression space 10 with a self-controlled nozzle device 20, 22, 24. The liquid to be sprayed is transported via a high-pressure pipe 32 from the high-pressure pump 30. This pump may be a reciprocating or gear pump. The compression space or chamber 10 is arranged in a pressure vessel 12, which space or chamber is connected to the high-pressure pipe 32 via a channel 14. In the example shown, the chamber 10 is cylindrical in shape, and its limits are defined by a piston 16 which is conical in shape and which closes the opening 22 of the pressure vessel 12. The piston 16 is movable in the housing 12 and is under the influence of an active force, for instance, a spring 17 and a screw 18 by which the spring can be regulated. The transported liquid reaches a high pressure, which is regulated by the spring 17 supported by the plate 19 and the piston 16, such that the active force of the spring 17 pushes the piston 16 against the opening 22 of the pressure vessel. When the highly compressed liquid in the space 10 passes the opening 22, the explosive process sets in as a result of the difference in pressure between the compression prevalent in the chamber 10 and the external pressure found past the opening 22. The opening 22 preferably has a diameter between 0.1 and 0.25 mm, while the pressure piston 16 active in the pressure vessel 12 has a diameter of 6 mm. If the piston is larger the opening 22 may also be larger.

It is possible to position the limited space 10 directly at the pump 30. The liquid before being explosively atomized has a pressure of 300 to $800 \times 10^5$ Pa or even greater. The resultant cloud is so homogenous and fine that it is not necessary to filter off larger particles. It is also possible to employ a larger amount of openings 22 in connection with the movable piston and its closing section 24. However, the cross sections of a larger amount of openings together should not be greater than the cross section of the one opening.

The apparatus further comprises a cloud chamber 40 in the form of a hollow cylinder with a detachable top and bottom. The nozzle 20 is arranged at the bottom of the cloud chamber 40 so as to allow the liquid to be atomized into the cloud chamber. The cloud chamber is preferably made of plastic such as acryl and has a wall thickness of about 1 cm. In view of the fact that it is easy to detach and reattach the top and the bottom, the cloud chamber can be cleaned without difficulty.

Close to or at the bottom, there is provided an air inlet 42, close to or at the top an air outlet 48. A first sound absorber 44 is arranged at the air inlet 42, which sound absorber comprises inter alia a dust filter 46 in its interior and serves both the purposes of air filtration and sound insulation. A second sound absorber 50 is arranged at the air outlet 48, which sound absorber also serves the purpose of sound insulation. The noise caused by the controllable nozzle can be advantageously absorbed by the sound absorbers. The second sound absorber 50 essentially consists of a hollow cylinder, whose diameter is smaller than that of the cloud chamber 40, whose bottom and top have an opening each. Further disk-shaped screens are arranged in the interior of the hollow cylinder, which screens have a small opening each. The openings at the bottom and at the top as well as the openings in the disk-shaped screens are staggered based on the center line of the sound absorber, so that the air let out from the cloud chamber 40 through the sound absorber 50 is not emitted in a straight but in a winding course. A mouthpiece is connected to the outlet of the sound absorber 50 via a tube 56. A valve 62 is arranged in the interior of the mouthpiece 60, which opens one way, i.e., when the air is let out from the cloud chamber 40 to the mouthpiece, and closes the other way. This is to advantageously avoid that external air such as, for example, expired air gets back from the mouthpiece into the cloud chamber.

The presently disclosed embodiment is therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for dispensing atomized liquid substances for inhalation comprising:
    a. compressing the liquid substance to be atomized at a pressure of $300 \times 10^5$ Pa to $800 \times 10^5$ Pa so that the liquid substance decreases in volume;
    b. explosively releasing the compressed liquid substance to the normal atmosphere at a pressure of $1 \times 10^5$ Pa, for causing the liquid substance to burst into extremely small particles; and
    c. repeating steps a and b preferably several times.

2. A method as in claim 1 wherein the liquid substance is one of the bicompatible substances selected from the group consisting of vitamin A, vitamin B, vitamin C, vitamin E, lecithin, and mixtures thereof.

3. A method as in claim 2 wherein 0.5 to 5% by weight of vitamin A and/or 0.5 to 5% by weight of vitamin E are used.

4. A method as in claim 1 wherein the liquid substance is a viscous liquid.

5. A method as in claim 4 wherein compression takes place at a pressure of $550 \times 10^5$ Pa.

6. The method of claim 4, wherein said viscous liquid is oil.

7. A method as in claim 1 wherein the liquid substance is vegetable oil.

8. The method as in claim 7, wherein said vegetable oil is peanut oil.

9. A method as in claim 1 wherein the liquid substance is peanut oil having 2.5% of vitamin A acetate and 4% of vitamin E tocopherol.

10. A method as in claim 1 wherein the liquid substance is peanut oil having 1.25% of vitamin A acetate and 0.5% of vitamin E tocopherol.

11. A method as in claim 1 wherein the liquid substance is a salt solution.

12. A method as in claim 11 wherein compression takes place at a pressure of $430 \times 10^5$ Pa.

13. A method as in claim 1 wherein the resultant particles are about 0.5 to about 10 $\mu m^3$ in size.

14. A method as in claim 13 wherein the resultant particles all have the same electrical charge.

15. The method of claim 13, wherein the resultant particles are about 1 $\mu m^3$ in size.

16. A method as in claim 1 wherein about 0.25 ml of liquid substance is atomized in each of steps a and b.

17. An apparatus for dispensing atomized liquid substances for inhalation comprising:
    a. a compression means having a space for compressing the liquid substance to be atomized to a pressure of about $300 \times 10^5$ Pa to about $800 \times 10^5$ Pa so that the liquid substance decreases in volume and
    b. at least one controllable nozzle for explosively releasing the compressed liquid substance from the compression liquid substance from the compression space into the normal atmosphere at a pressure of $1 \times 10^5$ Pa, for causing the liquid substance to burst into extremely small particles.

18. An apparatus as in claim 17 which comprises a high-pressure pump which is connected to the compression space via a pipe.

19. An apparatus as in claim 18 wherein the controllable nozzle has at least a small opening and a closer which clears the opening depending on the pressure adjusted.

20. An apparatus as in claim 19 wherein the nozzle automatically opens at an adjustable upper pressure between 300 and $800 \times 10^5$ Pa and automatically closes at an adjustable lower pressure of 200 to $600 \times 10^5$ Pa.

21. An apparatus as in claim 20 wherein the nozzle is arranged at a cloud chamber such that the atomized particles are released into the cloud chamber.

22. An apparatus as in claim 21 wherein the cloud chamber has an air inlet and an air outlet.

23. An apparatus as in claim 22 wherein the air inlet is provided with a first sound absorber, and the air outlet with a second sound absorber.

24. An apparatus as in claim 23 wherein a mouthpiece is arranged at the air outlet.

25. An apparatus as in claim 24 wherein the mouthpiece has a non-return valve which opens when air is sucked from the cloud chamber.

* * * * *